United States Patent
Carter

(10) Patent No.: US 9,936,901 B2
(45) Date of Patent: Apr. 10, 2018

(54) SYNCHRONIZING ACCELEROMETER DATA RECEIVED FROM MULTIPLE ACCELEROMETERS AND DYNAMICALLY COMPENSATING FOR ACCELEROMETER ORIENTATION

(71) Applicant: Abaham Carter, Salt Lake City, UT (US)

(72) Inventor: Abaham Carter, Salt Lake City, UT (US)

( * ) Notice: Subject to any disclaimer, the term of this patent is extended or adjusted under 35 U.S.C. 154(b) by 609 days.

(21) Appl. No.: 14/184,597

(22) Filed: Feb. 19, 2014

(65) Prior Publication Data
US 2014/0236531 A1  Aug. 21, 2014

Related U.S. Application Data

(60) Provisional application No. 61/766,606, filed on Feb. 19, 2013.

(51) Int. Cl.
*A61B 5/11* (2006.01)
*G01C 22/00* (2006.01)

(52) U.S. Cl.
CPC .......... *A61B 5/1123* (2013.01); *G01C 22/006* (2013.01)

(58) Field of Classification Search
CPC ......... A61B 5/11; A61B 5/112; A61B 5/1118; A61B 5/1123; G01C 22/006
See application file for complete search history.

(56) References Cited

PUBLICATIONS

Bannach et al., Automatic Event-Based Synchronization of Multimodal Data Streams from Wearable and Ambient Sensors, EuroSSC 2009, LNCS 5741, pp. 135-148.*

* cited by examiner

*Primary Examiner* — Toan Le
(74) *Attorney, Agent, or Firm* — Michael F. Krieger; Kirton McConkie

(57) ABSTRACT

Accelerometer data that is received from multiple accelerometers can be synchronized to identify a known movement. This synchronization occurs in real time as the accelerometer data is received from the multiple devices. The orientation of an accelerometer can be compensated for dynamically. By dynamically compensating for the orientation, the user can wear the accelerometers in various orientations without needing to calibrate a portable computing device to account for a particular orientation. Portable devices can have one or more detachable accelerometers. The accelerometers can be detached and placed at virtually any location of a user's body to allow for the detection of custom movements.

20 Claims, 15 Drawing Sheets

SYNCHRONIZING ACCELEROMETER DATA RECEIVED FROM MULTIPLE ACCELEROMETERS AND DYNAMICALLY COMPENSATING FOR ACCELEROMETER ORIENTATION

CROSS-REFERENCE TO RELATED APPLICATIONS

This application claims the benefit of U.S. Provisional Patent Application No. 61/766,606 which was filed on Feb. 19, 2013.

BACKGROUND

Many devices have been developed for use during exercise to track various parameters of a user's workout. For example, GPS watches can track the total distance traveled by the user, pedometers can count a number of steps a user takes, heart rate monitors can track a user's heart rate, etc.

Many of these devices employ accelerometers to detect a particular movement. For example, pedometers can use an accelerometer to detect the acceleration caused when a user takes a step. In such devices, a single accelerometer is used to generate accelerometer data that can be processed on the device itself or relayed to another device for processing.

BRIEF SUMMARY

The present invention extends to methods, systems, and computer program products for synchronizing accelerometer data that is received from multiple accelerometers. This synchronization occurs in real time as the accelerometer data is received from the multiple devices. In this way, complex motions can be detected and distinguished from other motions.

The present invention also extends to methods, systems, and computer program products for dynamically compensating for the orientation of an accelerometer. By dynamically compensating for the orientation, the user can wear the accelerometers in various orientations without needing to calibrate a portable computing device to account for a particular orientation.

The present invention also extends to portable devices having one or more detachable accelerometers. The accelerometers can be detached and placed at virtually any location of a user's body to allow for the detection of custom movements.

This summary is provided to introduce a selection of concepts in a simplified form that are further described below in the Detailed Description. This Summary is not intended to identify key features or essential features of the claimed subject matter.

Additional features and advantages of the invention will be set forth in the description which follows, and in part will be obvious from the description, or may be learned by the practice of the invention. The features and advantages of the invention may be realized and obtained by means of the instruments and combinations particularly pointed out in the appended claims. These and other features of the present invention will become more fully apparent from the following description and appended claims, or may be learned by the practice of the invention as set forth hereinafter.

BRIEF DESCRIPTION OF THE DRAWINGS

In order to describe the manner in which the above-recited and other advantages and features of the invention can be obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION

Figure 1:
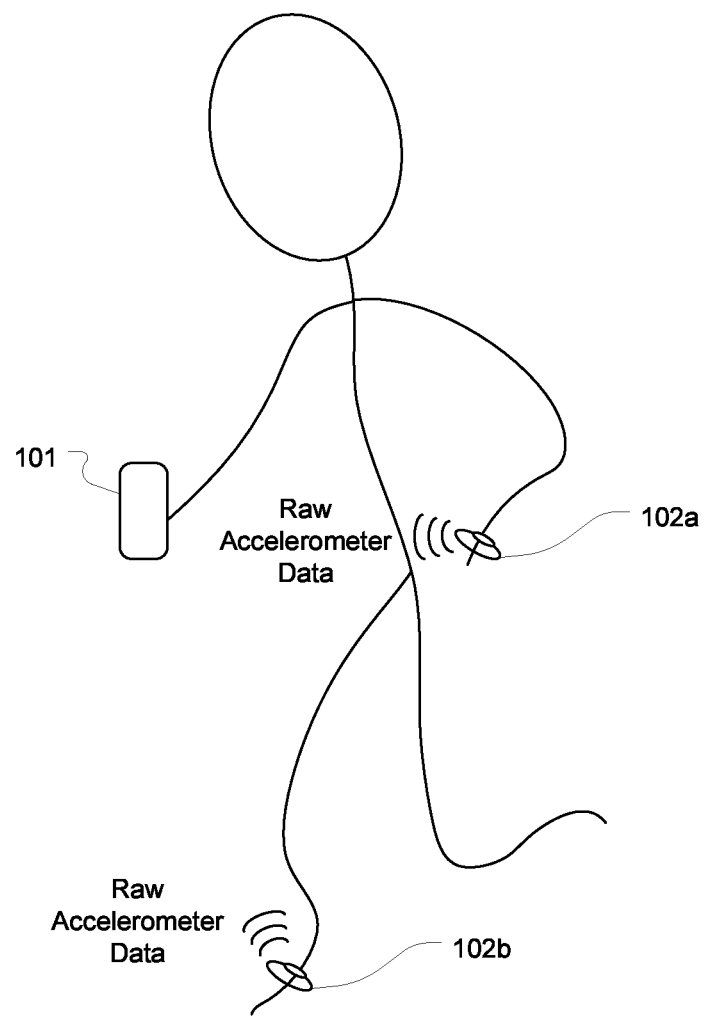
FIGS. 1 and 2 illustrate exemplary computing environments in which the present invention can be implemented.

The present invention extends to methods, systems, and computer program products for synchronizing accelerometer data that is received from multiple accelerometers. This synchronization occurs in real time as the accelerometer data is received from the multiple devices. In this way, complex motions can be detected and distinguished from other motions.

The present invention also extends to methods, systems, and computer program products for dynamically compensating for the orientation of an accelerometer. By dynamically compensating for the orientation, the user can wear the accelerometers in various orientations without needing to calibrate a portable computing device to account for a particular orientation.

The present invention also extends to portable devices having one or more detachable accelerometers. The accelerometers can be detached and placed at virtually any location of a user's body to allow for the detection of custom movements.

Embodiments of the present invention may comprise or utilize special purpose or general-purpose computers including computer hardware, such as, for example, one or more processors and system memory, as discussed in greater detail below. Embodiments within the scope of the present invention also include physical and other computer-readable media for carrying or storing computer-executable instructions and/or data structures. Such computer-readable media can be any available media that can be accessed by a general purpose or special purpose computer system.

Computer-readable media is categorized into two disjoint categories: computer storage media and transmission media. Computer storage media (devices) include RAM, ROM, EEPROM, CD-ROM, solid state drives ("SSDs") (e.g., based on RAM), Flash memory, phase-change memory ("PCM"), other types of memory, other optical disk storage, magnetic disk storage or other magnetic storage devices, or any other similarly storage medium which can be used to store desired program code means in the form of computer-executable instructions or data structures and which can be accessed by a general purpose or special purpose computer. Transmission media include signals and carrier waves.

Computer-executable instructions comprise, for example, instructions and data which, when executed by a processor, cause a general purpose computer, special purpose computer, or special purpose processing device to perform a certain function or group of functions. The computer executable instructions may be, for example, binaries, intermediate format instructions such as assembly language or P-Code, or even source code.

Those skilled in the art will appreciate that the invention may be practiced in network computing environments with many types of computer system configurations, including, personal computers, desktop computers, laptop computers, message processors, hand-held devices, multi-processor systems, microprocessor-based or programmable consumer electronics, network PCs, minicomputers, mainframe computers, mobile telephones, PDAs, tablets, pagers, routers, switches, and the like.

The invention may also be practiced in distributed system environments where local and remote computer systems, which are linked (either by hardwired data links, wireless data links, or by a combination of hardwired and wireless data links) through a network, both perform tasks. In a distributed system environment, program modules may be located in both local and remote memory storage devices. An example of a distributed system environment is a cloud of networked servers or server resources. Accordingly, the present invention can be hosted in a cloud environment.

FIG. 1 illustrates an exemplary computer environment 100 in which the present invention can be implemented. Computer environment 100 includes a portable computing device 101 and portable accelerometer devices 102a, 102b that are worn by a user during a workout or other activity. In a typical implementation, portable computing device 101 can be a user's smart phone or other device capable of running a mobile application (e.g. an MP3 player or tablet). Portable accelerometer devices 102a, 102b are shown in FIG. 1 as being in the form of a bracelet worn around the user's wrist or ankle. However, any other type of portable device that includes an accelerometer can be used. For example, portable accelerometer device 102b can comprise a shoe clip or other component that attaches to the user's shoe.

Although FIG. 1 depicts two portable accelerometer devices 102a, 102b being worn around the wrist and on the foot respectively, the present invention is not limited to any specific number of portable accelerometer devices or any particular placement of the portable accelerometer devices on the user's body. For example, one or more portable accelerometer devices can be worn on the elbow, hip, knee, head, etc.

Figure 2:
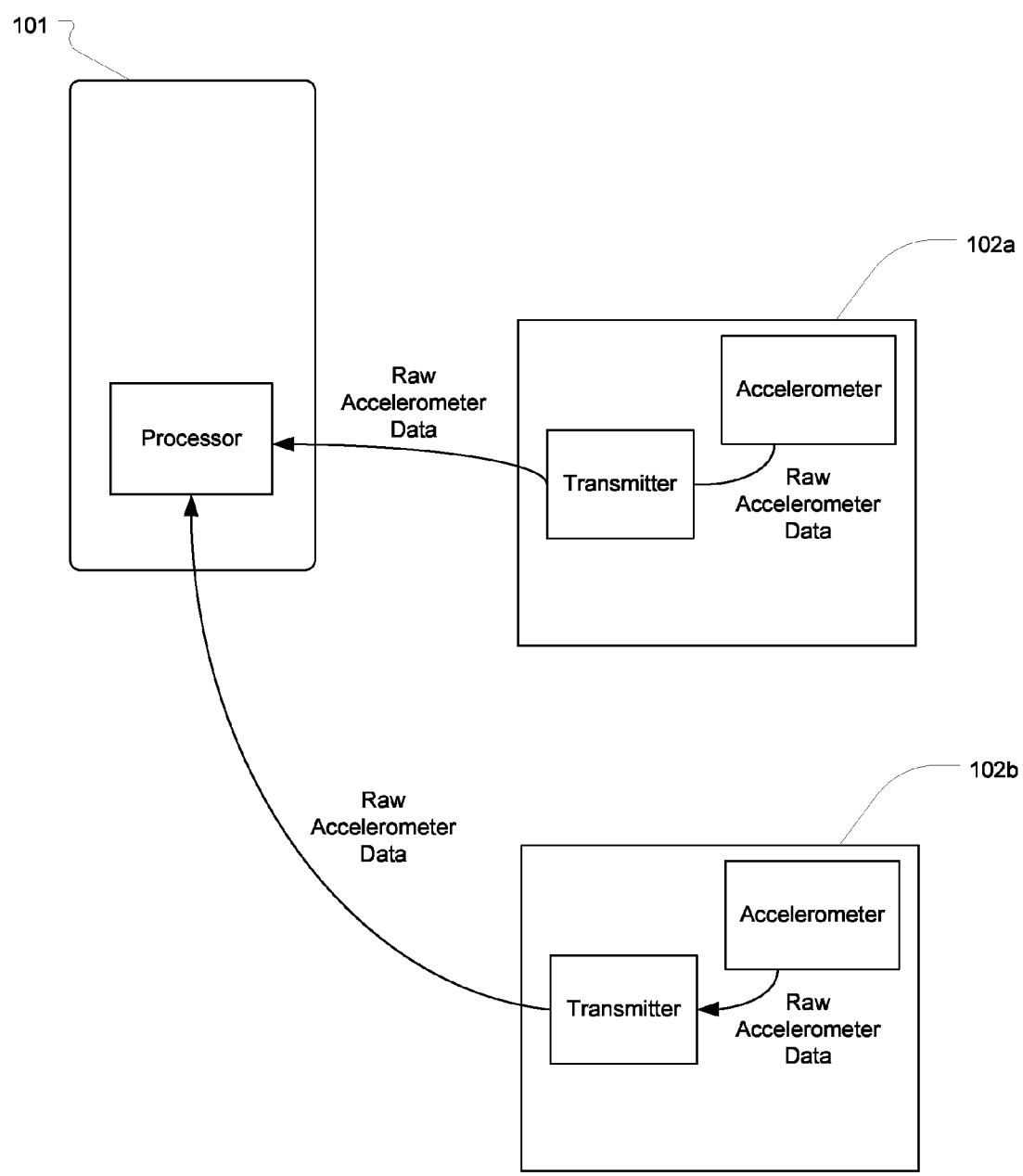

FIG. 2 illustrates an example configuration of portable computing device 101. As shown, portable computing device 101 contains a processor 201 and a database 200. Processor 201 is configured to receive accelerometer data from one or more accelerometers (e.g. accelerometers 102a, 102b). Database 200 contains stored accelerometer data representing particular movements. When processor 201 receives accelerometer data from one or more accelerometers, processor 201 can access the stored accelerometer data in database 200 to attempt to match the received accelerometer data to the stored accelerometer data representing a particular movement. If a match is found, processor 201 can store an indication that the user has performed the particular movement.

Figure 3A:
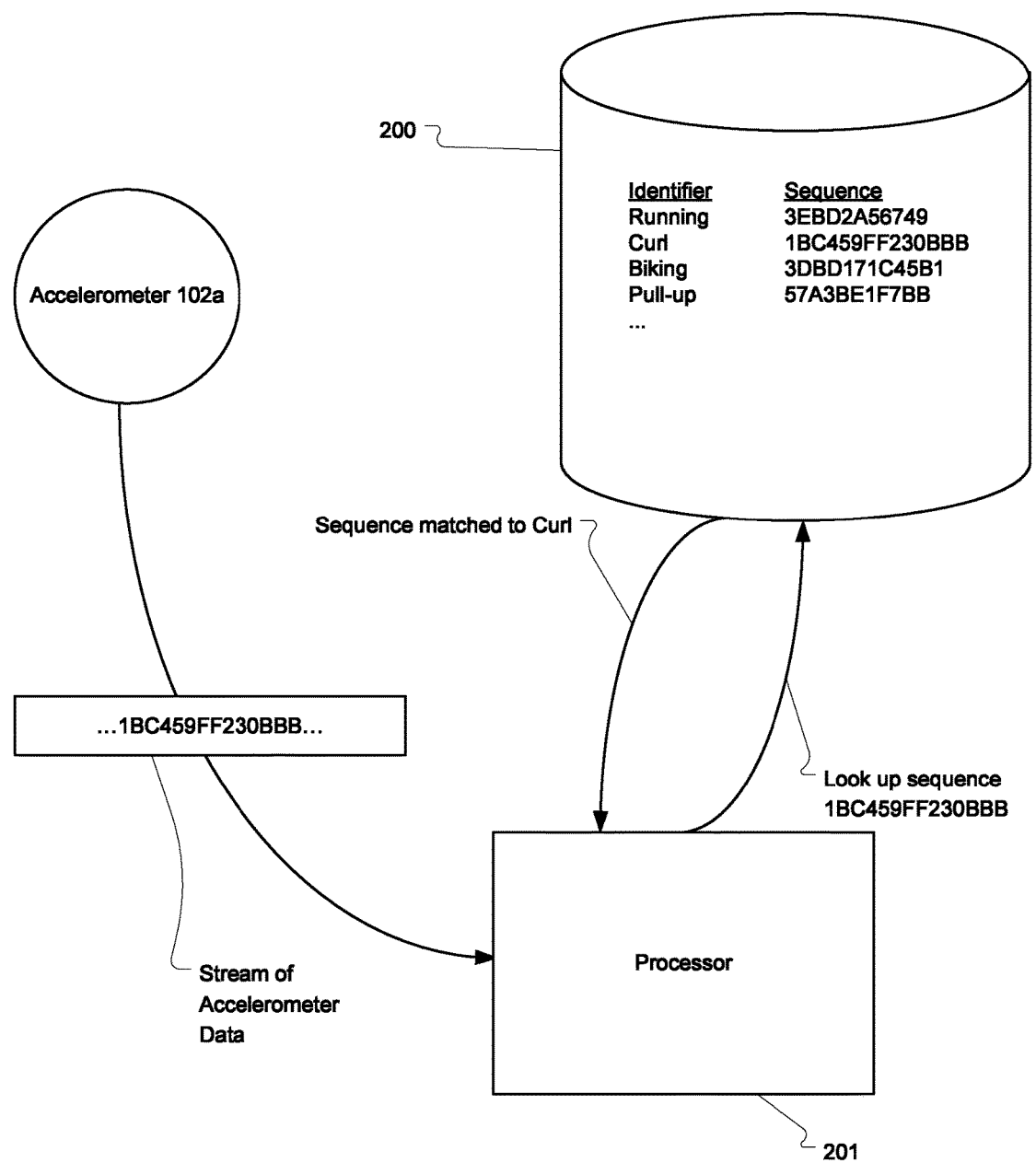
FIGS. 3A-3C illustrate examples of how accelerometer data can be matched to known movements.
Figure 3B:
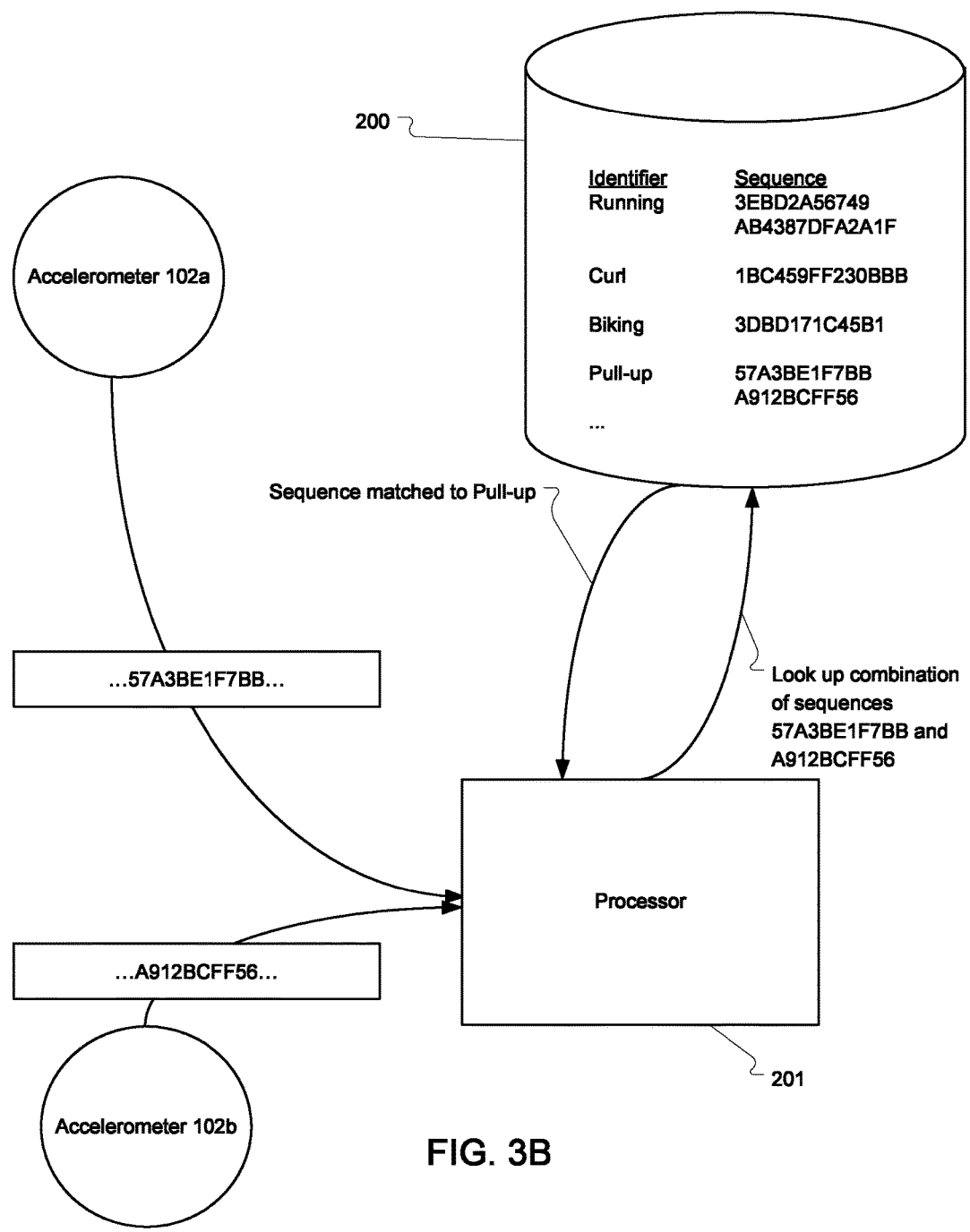

FIGS. 3A and 3B illustrate a simplified example of how this matching can be performed. This simplified example illustrates the direct matching of accelerometer data to known sequences of accelerometer data. However, as further described below, this matching can also be performed by first processing the raw accelerometer data into a more useful format for comparison.

FIG. 3A shows a single accelerometer transmitting a stream of accelerometer data which is received by processor 201. Database 200 is shown as storing various sequences with an associated identifier. Database 200 can be built using known sequences that identify a particular movement. For example, database 200 can be installed on a mobile phone as part of a mobile app.

As mentioned, the depicted sequences in database 200 are simplified to better illustrate the process by which the matching occurs. However, in many cases, rather than a single sequence, a range of sequences or even logic that identifies whether a received sequence matches a particular movement can be used. One specific example of how the data can be stored in database 200 is provided below with respect to FIG. 3C.

When processor 201 receives or identifies a sequence in the accelerometer data from accelerometer 102a (which in this example is 1BC459FF230BBB), processor 201 can perform a look-up to identify whether the received sequence matches any stored sequence in database 200. Because the received sequence matches the stored sequence corresponding to Curl, processor 201 can know that the user has performed a curl. Once it is determined that the user has performed a curl, processor 201 can perform various actions such as updating a count of the number of curls performed, updating a display, generating a notification, etc.

FIG. 3B is similar to FIG. 3A but represents in simplified form how a particular movement can be determined using accelerometer data from multiple accelerometers. As shown, both accelerometers 102a and 102b are transmitting accelerometer data representing the movement of the user's body on which each accelerometer is placed.

As in FIG. 3A, processor 201 receives the accelerometer data and performs a look-up. In contrast to FIG. 3A, database 200 is shown as storing two sequences for some movements. For example, the entry for Running includes two sequences which represent the typical motion of an accelerometer attached to the user's shoe and of an accelerometer attached to the user's wrist. The entry for Pull-up likewise includes two sequences.

It is noted that, although only two sequences are shown, it is possible to use more than two sequences for some movements (e.g. when an exercise involves distinct movement of more than two body parts). Also, for some exercises, accelerometer data from only one accelerometer may be required to identify the exercise even if the user is wearing multiple accelerometers. For example, because the user's foot generally remains stationary during a curl (and because it may not be necessary or desirable to identify leg movement during a curl), only one sequence may be stored that represents accelerometer data from an accelerometer on the user's wrist, hand, or arm.

Whether processor 201 receives data from one, two, or more accelerometers, processor 201 can perform a look-up using any or all of the received data. In FIG. 3B, the look-up is performed using sequences 57A3BE1F7BB and A912BCFF56 which match the stored sequences for a pull-up. Accordingly, processor 201 knows that the user has performed a pull-up and can respond accordingly. In another example, if the received accelerometer data had included sequences of 3 DBD171C45B1 and 1276BBB34, the lookup could have matched only one of the sequences (the first sequence) which would have identified that the user is pedaling a bike.

In some embodiments, the particular movements identified in database 200 can be highly granular. For example, database 200 can include an entry identifying Running and an entry identifying Running While Pushing A Jogging Stroller. In this example, the entries may contain the same or similar sequence representing the motion of the user's leg while running (e.g. identifying a step), and a sequence representing the motion of the user's arm in each case (e.g. swinging in the case of Running, and stationary in the case of Running While Pushing A Jogging Stroller). Similar distinctions can be made with other types of exercises (e.g. a standard pull-up versus a cross-fit type swinging pull-up).

Figure 3C:
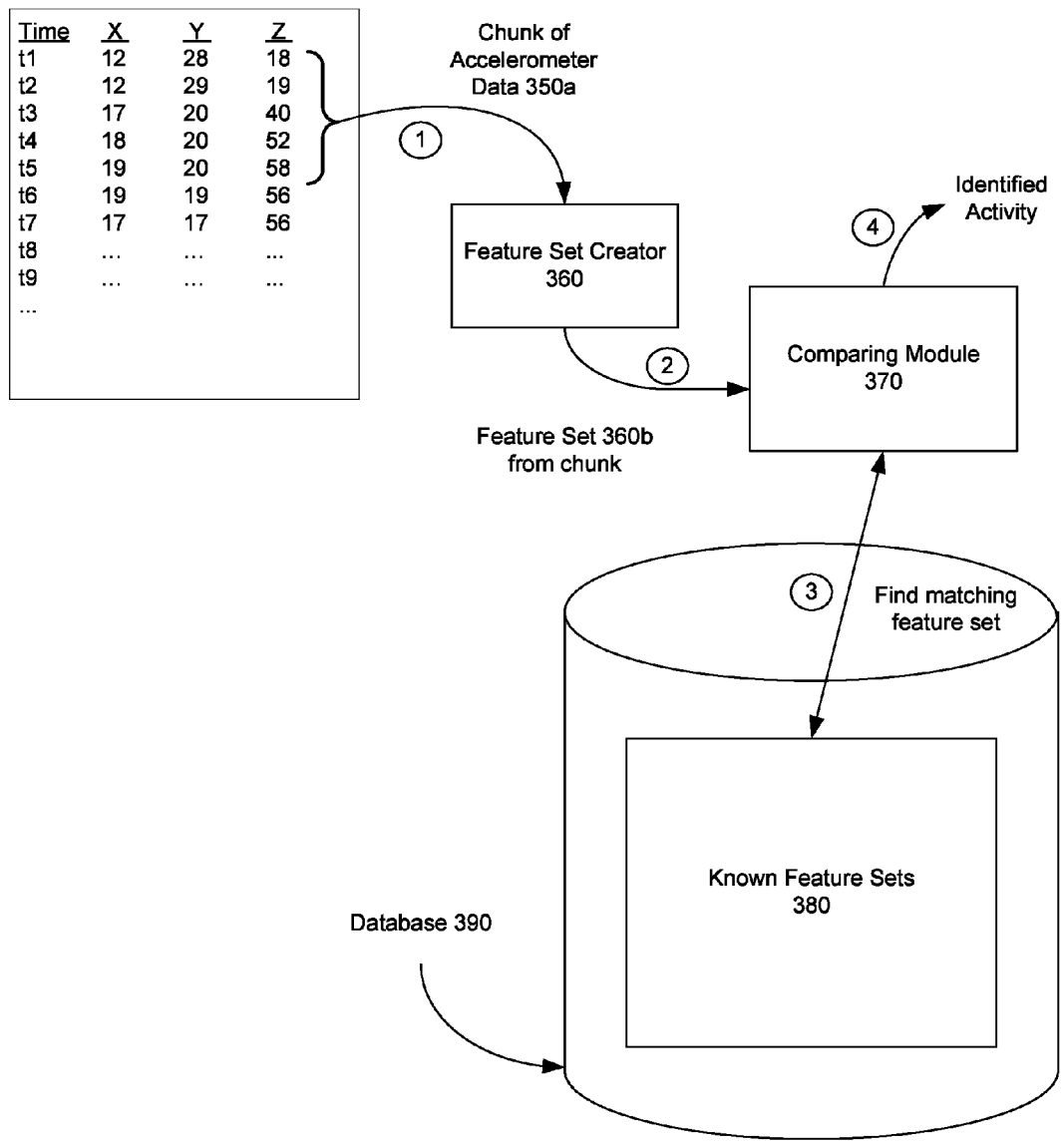

FIG. 3C illustrates a particular example configuration of a portable computing device 101 that can be used to implement the present invention. The numbers used to describe accelerometer data in FIG. 3C are exemplary and have been chosen to simplify the description of the invention. However, the specific format used in the described processes can vary as desired.

FIG. 3C shows an example data stream 350 that is received from an accelerometer. In this example, it is assumed that a single accelerometer is being used. However, similar processing can be performed on the data received from one or more other accelerometers.

FIG. 3C represents a general description of the process of converting the data 350 into a feature set that is compared to known feature sets 380 to identify an activity being performed. Data 350 is shown as comprising three axes (x, y, z) of accelerometer readings over a number of time periods (t1-t9).

The first step of the depicted process is to divide data 350 into various chunks. The division of data 350 into chunks can be based on many factors. In the example shown in FIG. 3C, a chunk 350a is shown as comprising the accelerometer data received during the time interval t1-t4 (e.g. 4 seconds if a time period is 1 second, 2 seconds if a time period is 0.5 seconds, etc.). The second step comprises feature set creator 360 generating a feature set 360b from chunk 350a. The third step comprises comparing module 370 comparing feature set 360b to the known features sets 380 in database 390 to determine the known feature set that most closely matches feature set 360b. This closest matching feature set represents the activity being performed by the user. Finally, the fourth step comprises outputting the name of this identified activity.

Synchronizing Data Received from Multiple Accelerometers

When multiple accelerometers are used to identify an activity being performed by a user, it is necessary to process the appropriate accelerometer data received from each accelerometer. Specifically, because accelerometer data generated by the accelerometers at the same time may not be received or otherwise available for processing at the portable computing device at the same time, it can be necessary to synchronize the accelerometer data.

Figure 4:
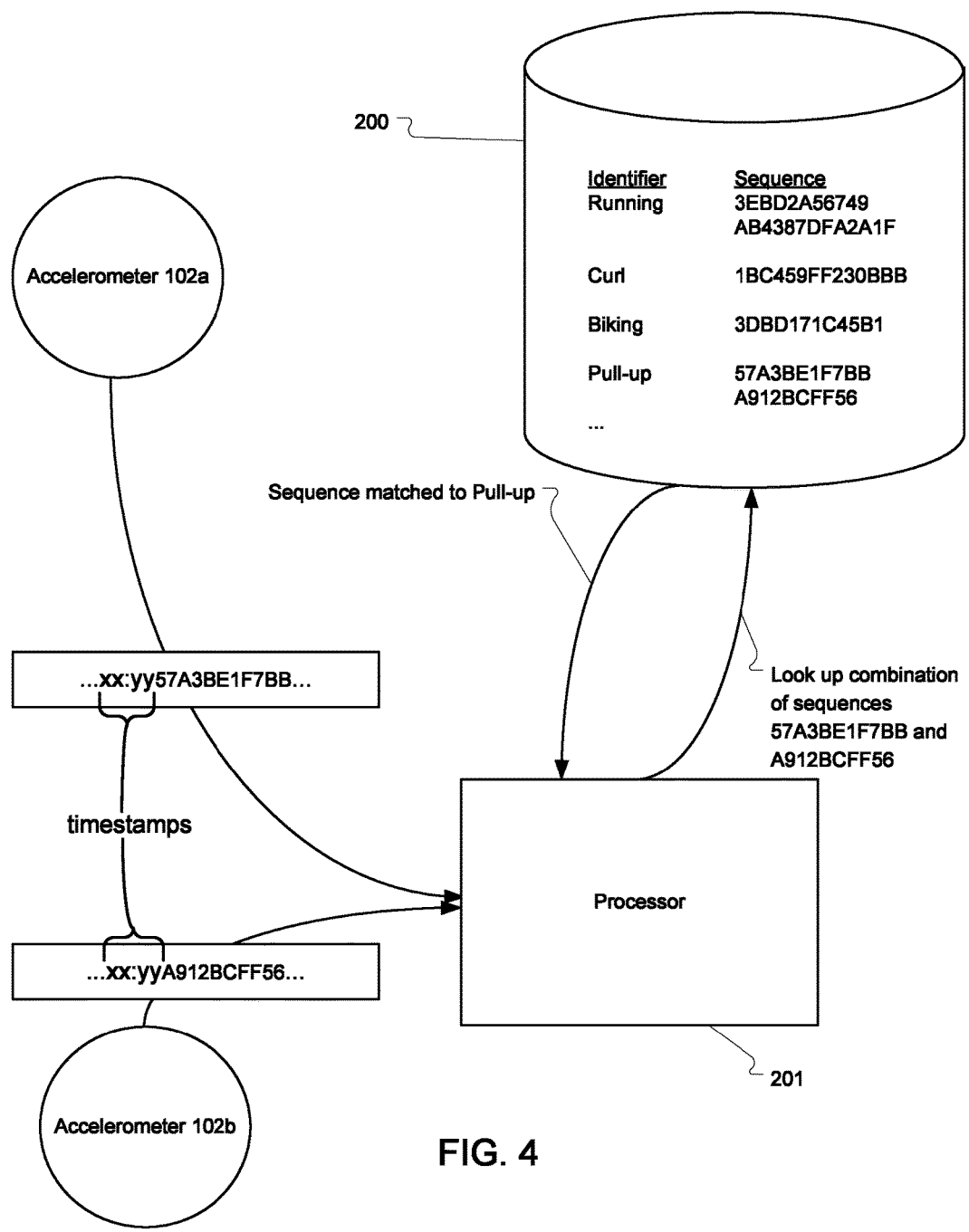
FIG. 4 illustrates an example of how timestamps can be used to synchronize accelerometer data received from multiple accelerometers.

FIG. 4 illustrates one example of how this synchronization can be performed. FIG. 4 is similar to FIG. 3B with the addition of a timestamp to each sequence of accelerometer data (shown as xx:yy appended to the beginning of each sequence). The example timestamp used in FIG. 4 is a simplified example to facilitate illustration, and any suitable format for a timestamp can be used.

When processor 201 receives accelerometer data from each accelerometer 102a, 102b, prior to using the sequences to perform a look up for a matching sequence, processor 201 can first identify sequences from the multiple accelerometers that share a common timestamp. A common timestamp does not have to be an exact match, but should be close enough to ensure that accelerometer data that was generated as substantially the same time is being used together to identify a known movement.

Once processor 201 has identified sequences that share a common timestamp, the sequences can be used to query database 200 for a matching sequence to identify an activity being performed as is described above. Accordingly, the use of timestamps enables processor 201 to synchronize the streams of accelerometer data received from multiple accelerometers.

With respect to the example matching process shown in FIG. 3C, timestamps could also be used to synchronize the accelerometer data. For example, each chunk of accelerometer data (or each reading at each time interval) can include a timestamp. In this way, each feature set generated from received accelerometer data can include a timestamp to allow the feature sets generated from accelerometer data received from multiple accelerometers to be synchronized.

This synchronization can occur at various steps of the process depicted in FIG. 3C. For example, synchronization can occur prior to the chunk creation step, during the chunk creation step, or during the feature set creation step.

Figure 8A:
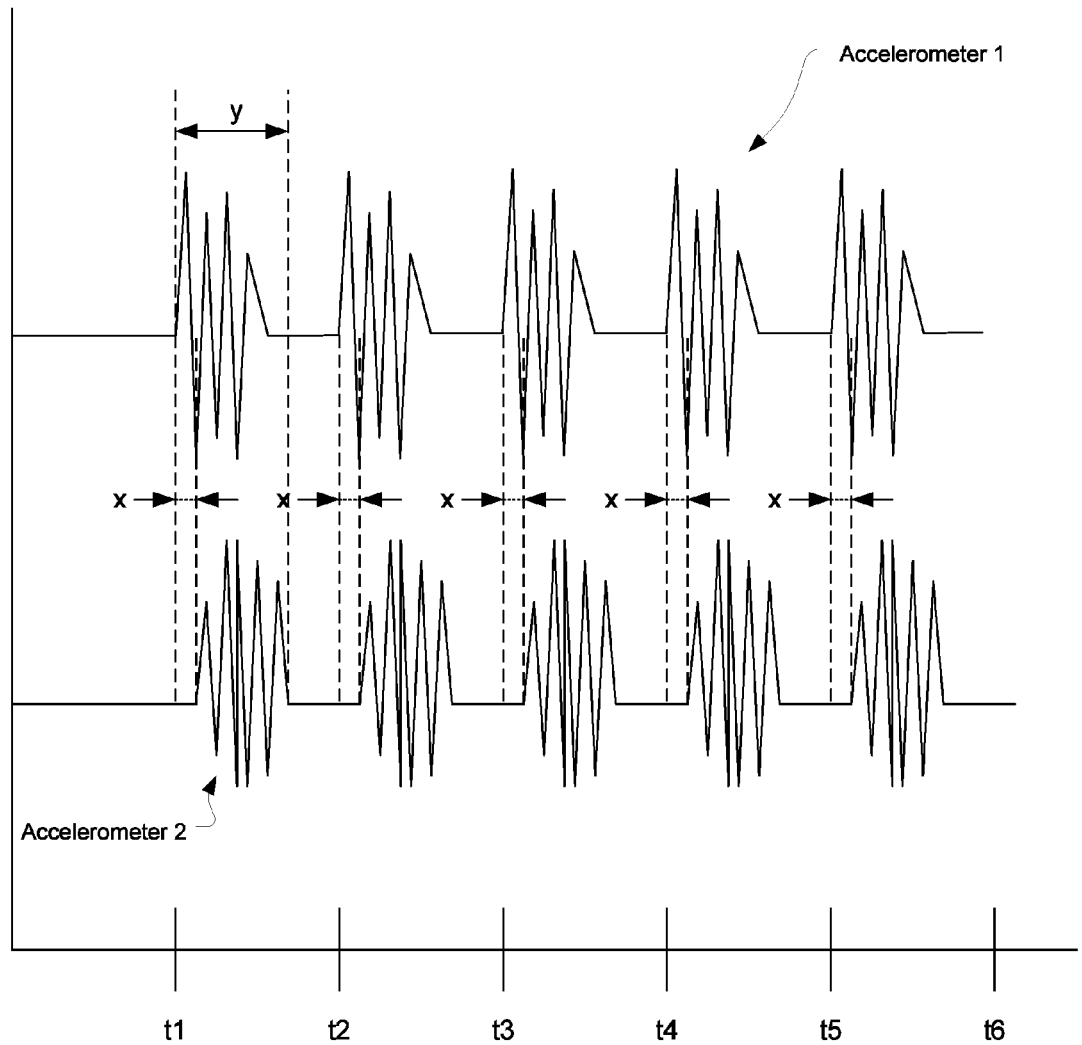
FIGS. 8A-8C represent how multiple streams of accelerometer data can be aligned.

In some cases, even with the use of timestamps, variations may exist between the accelerometer data received from multiple accelerometers. These variations (or misalignments) may lead to errors in identifying an activity being performed or, more likely, to errors in determining how many reps of an activity is being performed FIG. 8A illustrates an example of how accelerometer data that includes timestamps received from two accelerometers can be misaligned. FIG. 8A plots example accelerometer data received from two accelerometers (Accelerometer 1 and Accelerometer 2). Each set of accelerometer data includes timestamps. The plot shows that, based on the timestamps, the accelerometer data received from Accelerometer 1 indicates that activity occurred beginning at each of times t1, t2, t3, t4, and t5. For simplicity, the same graph (representing the accelerometer data) is shown repeated at each of these times. However, in a typical scenario, the graph will be different. For example, if the user is wearing the accelerometers at work, the activity at each of times t1-t5 may represent a different duration of time when the user got up and walked around the office.

Assuming FIG. 8A depicts accelerometer data generated while the user is walking at five different times during the day, the accelerometer data can be used to count the total number of steps the user is taking during each of these times. One problem that arises when the accelerometer data received from multiple devices is not aligned is that an incorrect number of repetitions may be counted. FIG. 8A illustrates how this error can occur. As shown, for any number of reasons, the timestamps from Accelerometers 1 and 2 can become misaligned. More specifically, even though the activity as detected by both accelerometers began at the same time (i.e. both accelerometers are reporting walking), the accelerometer data from Accelerometer 1 indicates that the activity started at each of times t1 through t5 while the accelerometer data from Accelerometer 2 indicates that the activity started at each of times t1 +x through t5 +x. Because of the misalignment, it appears as if the activity began at time t1 and continued for a duration of y (i.e. until the accelerometer data from Accelerometer 2 indicates that activity has ceased), when in fact the duration of the activity was only y−x.

Figure 8B:
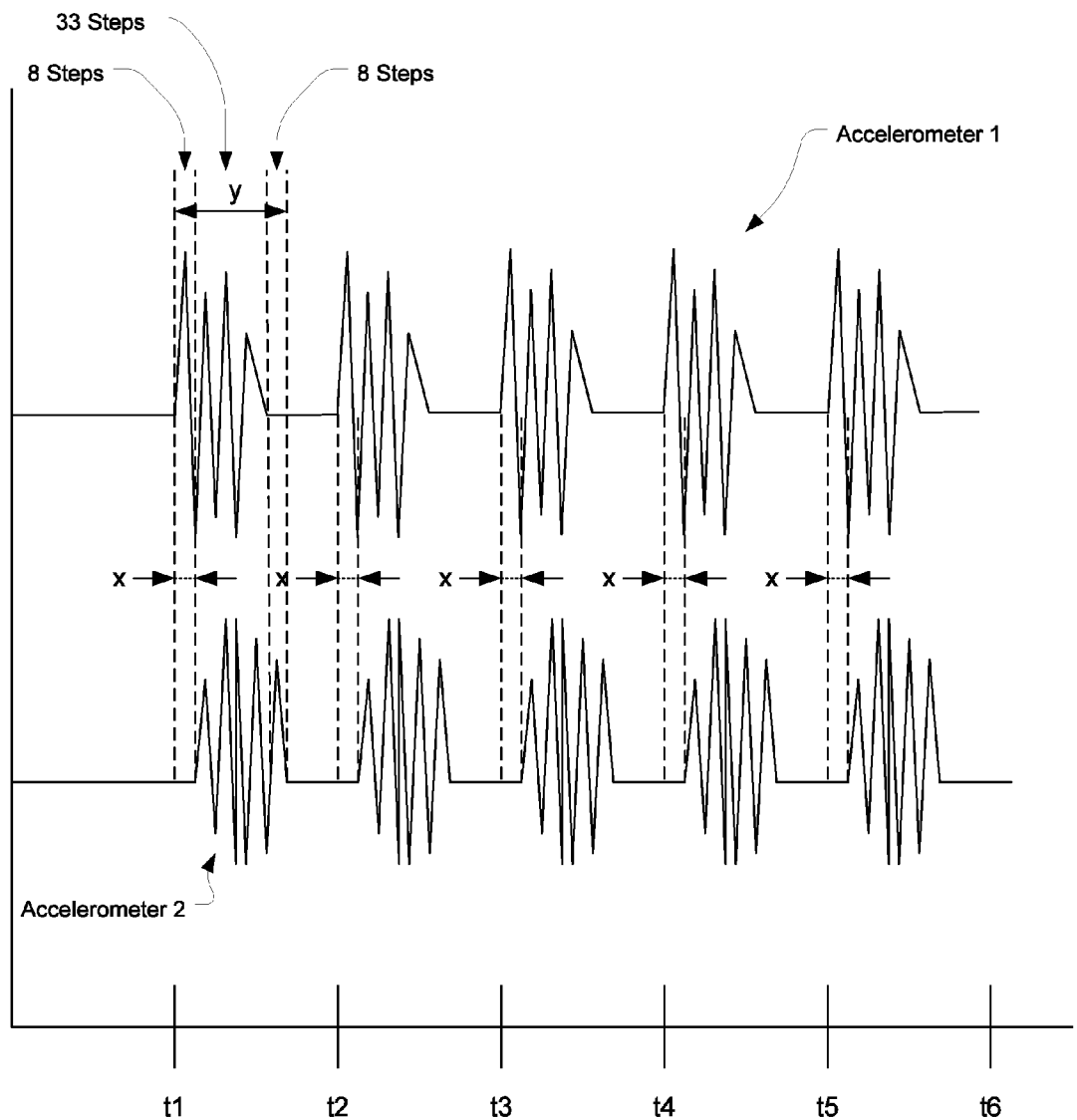

Because the accelerometer data from each accelerometer can independently be used to identify a step, too many steps may be counted. This is shown in FIG. 8B. Beginning at time t1 and for the duration x, a number of steps (8) may be calculated based only on the accelerometer data received from Accelerometer 1. Then, beginning at time t1 +x, a number of steps (33) may be calculated based on the accelerometer data received from both Accelerometers 1 and 2. Finally, beginning at time t1 +y−x (i.e. the time when the accelerometer data received from Accelerometer 1 indicates that activity has stopped), a number of steps (8) may be calculated based on the accelerometer data received only from Accelerometer 2. Without accounting for the misalignment, the total number of steps counted for the activity that started at time t1 will therefore be 49 (8+33+8) when in fact the total number of steps taken was only 41 (8+33).

In embodiments of the invention, this error caused by the misalignment of accelerometer data received from multiple accelerometers can be accounted for by shifting the accelerometer data received from one or more devices. As shown, the accelerometer data received from Accelerometer 2 has been shifted backwards so that it is aligned with the accelerometer data received from Accelerometer 1. With the accelerometer data aligned, the apparent duration of the activity is z (which in this case is the same as y−x) and the total number of steps calculated is 41.

Figure 8C:
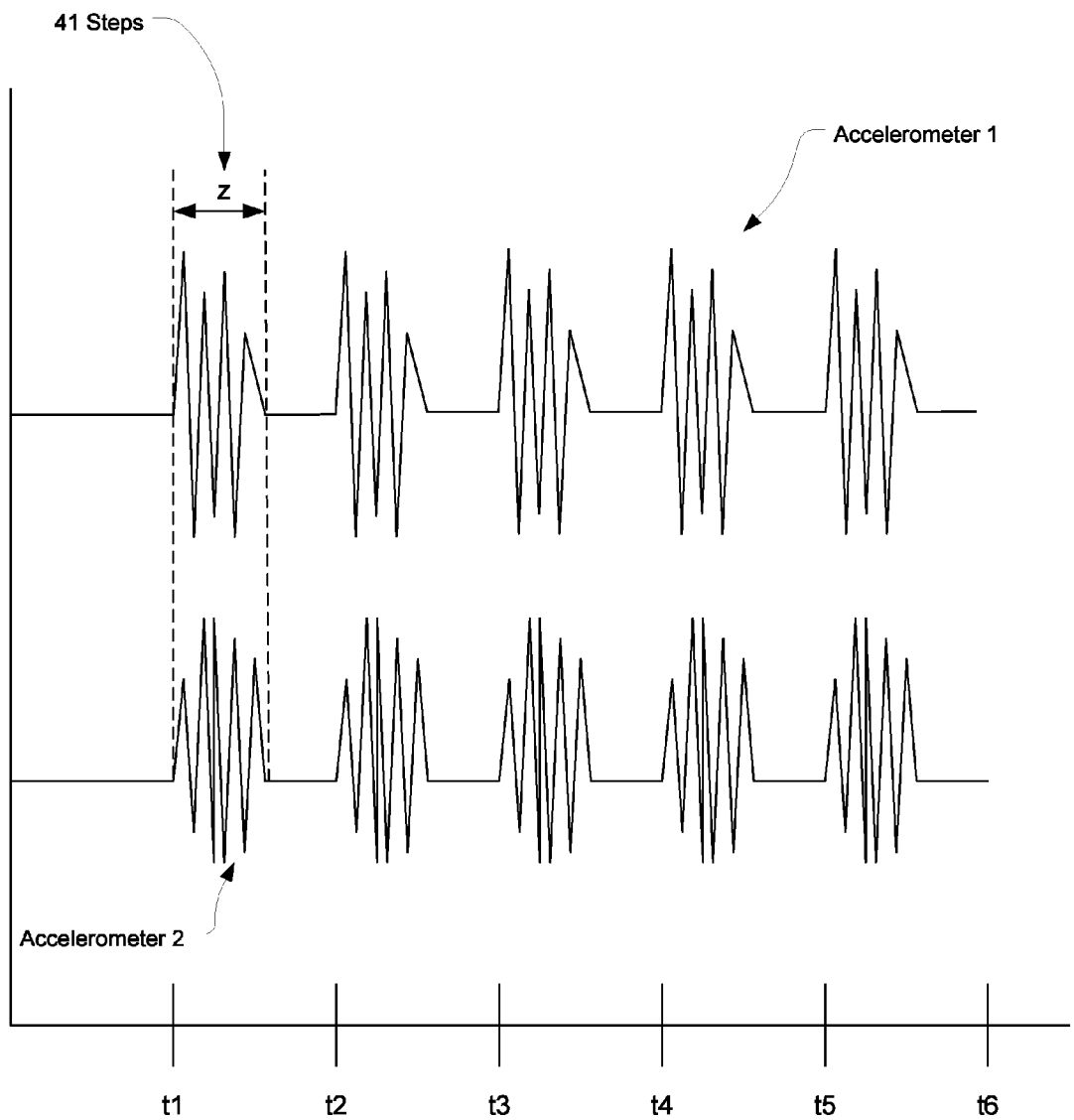

Although the example depicted in FIGS. 8A-8C indicates that the accelerometer data received over the entire plotted duration (i.e. from time t1 through time t5) was misaligned, the misalignment may only occur at a certain time (e.g. only between time t1 and t2). Therefore, the misalignment may only need to be accounted for at certain specific times.

To determine whether a misalignment has occurred, the accelerometer data received from each accelerometer can be processed independently. For example, if the accelerometer data received from Accelerometer 1 is independently processed, it can be determined that 41 steps occurred. The same is true of the accelerometer data received from Accelerometer 2. Once it is known that each of Accelerometers 1 and 2 independently identify the occurrence of 41 steps at approximately the same time, albeit at a different time, it can be assumed that a misalignment has occurred.

It is again noted that this misalignment can occur even when timestamps are used. For example, it is unlikely that each accelerometer will remain perfectly in sync with other accelerometers being worn by the user (e.g. due to clock skew (e.g. if each accelerometer assigns timestamps based on its internal clock), communication delays (e.g. if timestamps are assigned based on when the data is received by the master device or transmitted by the accelerometer), or other factors that may cause the generation of different timestamps by different devices for an activity performed at the same time). Even if the master device (e.g. a mobile phone) employs synchronization techniques, it is still possible that misalignments can occur. Accordingly, the present invention can increase the accuracy of identifying movements when accelerometer data from multiple accelerometers are used to report such movements.

The example depicted in FIGS. 8A-8C generalized the accelerometer data into a single axis. However, in many implementations, the accelerometer data will include data for each of the x, y, and z axes. In such cases, the accelerometer data for each axis can be processed independently as described above to determine whether a misalignment has occurred. In this way, misalignment can be accounted for even if the misalignment occurs between accelerometer data corresponding to different axes of the same accelerometer (e.g. between the x and y axes of the same accelerometer).

Because the example given in FIGS. 8A-8C only employed two streams of accelerometer data, the alignment could be achieved by simply shifting one stream into alignment with the other stream. However, when more than two streams are being processed (e.g. six streams when the x, y, and z axes each have their own stream or more when more than two accelerometers are used to track the same activity), it may be necessary to determine an amount to shift each stream to achieve alignment. In other words, it may be necessary to determine an offset for each stream which when applied causes all the streams to be in alignment. The process of aligning the streams of data can be carried out by determining a plurality of possible offsets to apply to each stream and then determining which set of offsets yields the greatest correlation among the various streams.

Accordingly, the present invention can account for misalignments that may occur in timestamps generated by multiple devices used to track the same activity. The occurrence of a misalignment can be determined by processing each stream of data independently and then correlating the streams in the best alignment. Once correlated and aligned, the multiple streams can be processed to identify a known movement as well as the number of repetitions of the known movement.

Dynamically Compensating for the Orientation of an Accelerometer

Regardless of the particular format used for data representing a movement (hereinafter referred to as a feature set), in some embodiments, more than one feature set may exist for the same movement. In some cases, the ability of a device to accurately identify a movement from accelerometer data can be dependent on the orientation of the one or more accelerometers generating the accelerometer data. For example, while running, the accelerometer data that is generated by an accelerometer bracelet may be different depending on which wrist the user is wearing the bracelet. Similarly, the accelerometer data may vary if the bracelet is worn with the accelerometer facing up as opposed to facing down.

Although different accelerometer data may be generated in such orientations, the device needs to identify that the user is running regardless of how the accelerometer is oriented. In other words, it may be overly burdensome to require the user to wear the accelerometer in a particular orientation (for which the accelerometer data is known for particular movements). The present invention addresses this concern by maintaining multiple feature sets for each known movement thereby allowing a movement to be identified regardless of the orientation in which the accelerometer is positioned.

Figure 5A:
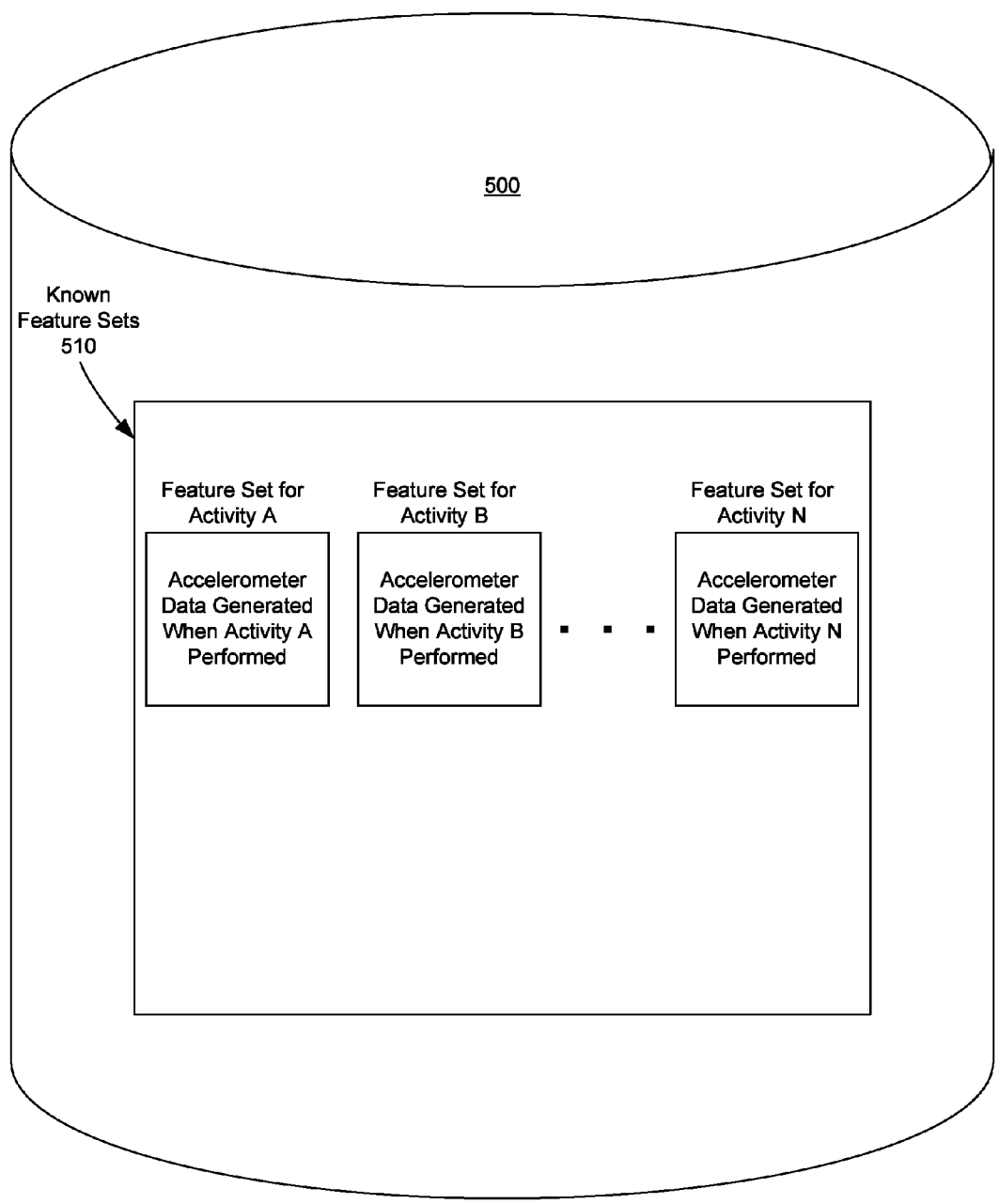
FIG. 5A illustrates an exemplary database that stores a single feature set for each known activity

FIG. 5A illustrates an example configuration of a database 500 where a single feature set is maintained for each known feature set (or known movement) 510. In such cases, for a device to accurately identify that the user is performing activity A, the received accelerometer data needs to match the stored feature set for activity A. As stated above, however, if the orientation of the one or more accelerometers is different than anticipated (e.g. if the user has the accelerometer upside-down), the accelerometer data may not match the feature set for activity A. The device may therefore be unable to identify that the user is performing activity A.

Figure 5B:
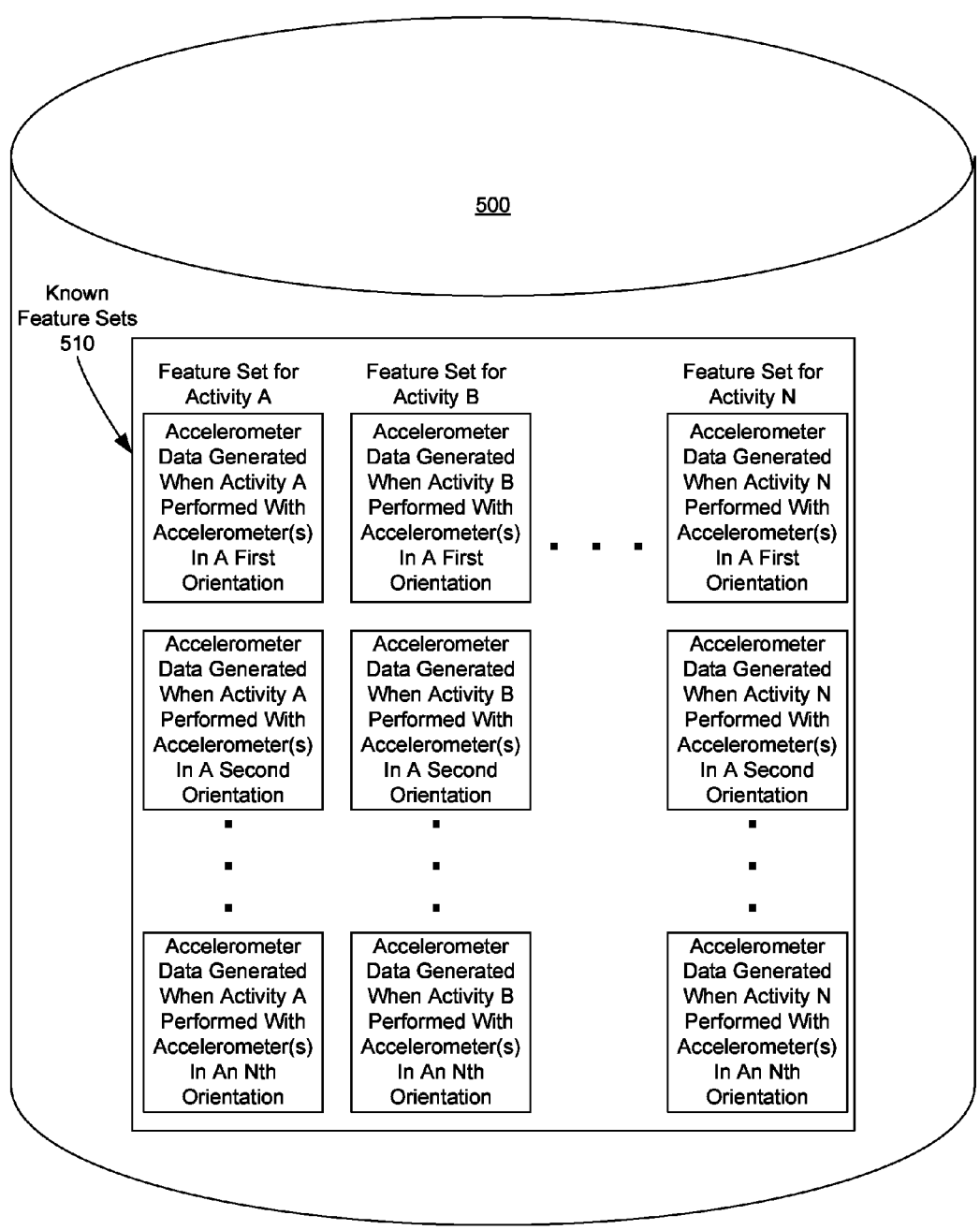
FIG. 5B illustrates an exemplary database that stores multiple feature sets for each known activity to allow for the detection of a movement regardless of the orientation of the one or more accelerometers.

FIG. 5B illustrates an example configuration of database 500 that can include multiple feature sets for some or all known activities so that the orientation of the accelerometer does not affect the ability to identify an activity. As shown, for each of the known activities, database 500 stores multiple feature sets. Each feature set for an activity may represent the accelerometer data that is generated when the one or more accelerometers are in a different orientation.

For any given activity, a different number of feature sets may be stored. For example, for one activity, there may be five different accelerometer orientations that will generate unique accelerometer data when the activity is performed. Therefore, five feature sets may be stored for the activity. In contrast, for another activity, there may be only two orientations that affect the accelerometer data generated during the activity. In such cases, two feature sets can be maintained. Likewise, if for an activity, the orientation does not matter, a single feature set can be maintained.

Figure 6A:
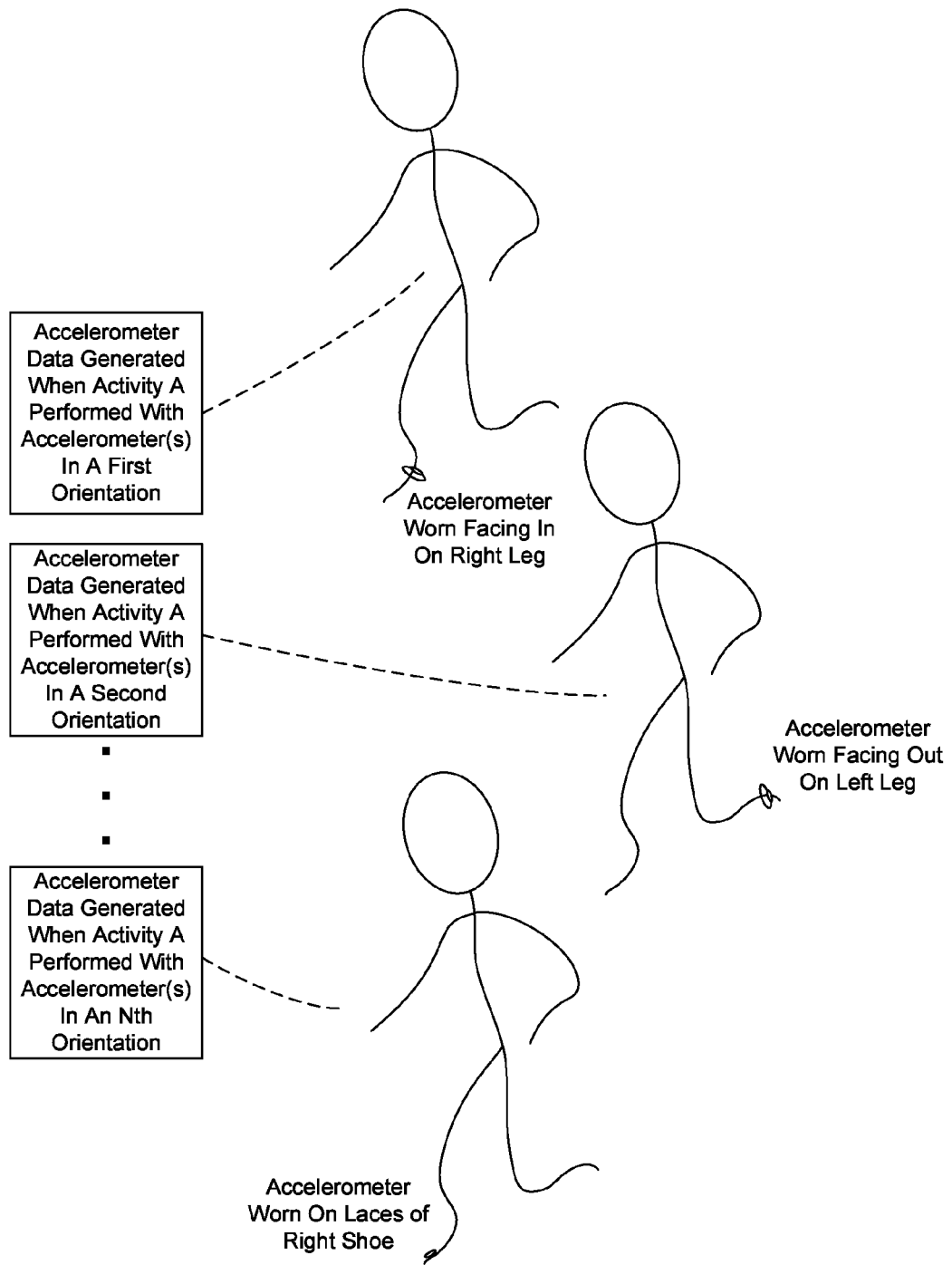
FIGS. 6A and 6B illustrate various orientations of an accelerometer.
Figure 6B:
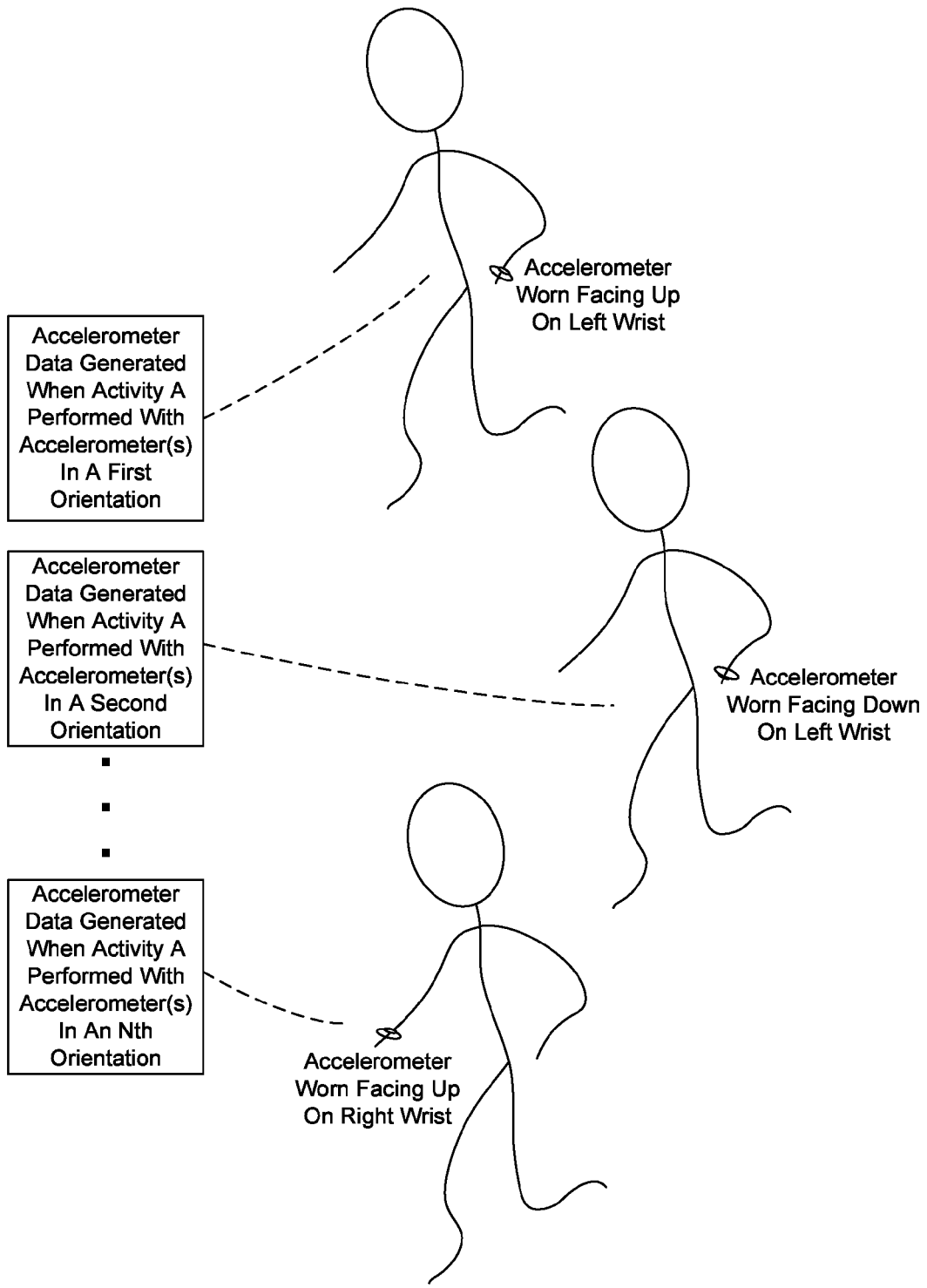

FIGS. 6A and 6B illustrate examples of the different orientations of an accelerometer as well as the matching of the accelerometer data to the same activity using multiple feature sets for the activity. Other orientations beyond those shown are equally possible.

FIG. 6A shows an accelerometer being worn at three different locations of the user's leg. At the top, the accelerometer is worn facing in on the right leg. In the middle, the accelerometer is worn facing out on the left leg. At the bottom, the accelerometer is worn on the laces of the right leg. In each case, the user is performing the same activity of running. As shown, the accelerometer data generated by the accelerometer in each of the three orientations is matched to a different feature set. However, each of these feature sets correspond to the same activity, and therefore, the device can accurately identify that the user is running FIG. 6B is similar to FIG. 6A except the accelerometer is being worn around the user's wrist.

Although FIGS. 6A and 6B illustrate that a feature set is identified using accelerometer data from a single accelerometer, accelerometer data from multiple accelerometers can be also used. In some embodiments, a unique feature set may exist for each combination of orientations of multiple accelerometers. However, in other embodiments, a second level of reference files can be used to minimize the number of feature sets that need to be stored.

Specifically, a reference file can exist for each orientation of a single accelerometer for each activity (i.e. a reference file can be similar to the feature sets as described above when a single accelerometer is used). If two accelerometers are used, a reference file can be identified that matches the data received from each accelerometer, and then a feature set that includes both identified reference files can be identified as the feature set of the activity being performed.

In a particular implementation of the invention, up to eight feature sets (or reference files) can be maintained for each activity. Using an example where the accelerometer is worn on the user's wrist, one file may exist for each of the following orientations: (1) on the right wrist facing up, (2) on the right wrist facing down, (3) on the left wrist facing up, (4) on the left wrist facing down, and (5)-(8) the same orientations as in (1)-(4) but when the arm is rotated 180 degrees (i.e. the arm is turned upside down). Similar orientations can exist for the accelerometer when worn on other parts of the body (e.g. on the right leg facing in or out, on the left leg facing in or out, etc.).

As mentioned above, these eight orientations may not be feasible or may be highly unlikely when the user performs some activities, and therefore, a feature set for less than the eight orientations may exist for those activities. In one example, fewer than eight orientations for an accelerometer worn on the wrist may be stored for a biking exercise because the user's wrist is unlikely to be turned upside down (and even if it were, the change in the accelerometer data may not render the data unidentifiable because the wrist remains generally stationary).

In some embodiments, rather than (or in addition to) storing feature sets for each possible orientation, the user can be provided the option to calibrate his device (e.g. his mobile phone) based on how the user is wearing the accelerometers. For example, after the user has attached the accelerometers to his body in a desired orientation, the device can prompt the user to remain still long enough for the device to receive accelerometer data from the accelerometers in their current orientation and to calibrate to the orientation. In some cases, this process can occur automatically without user involvement. For example, the device can use various algorithms to determine how the user is wearing the accelerometers and then compensate accordingly. The result of this calibration can be the creation of new feature sets or the creation of one or more algorithms to modify incoming data to match already stored feature sets.

In some embodiments, the user can be given the option to create new feature sets based on how he wears his accelerometers. In such cases, the user can specify the orientation of each accelerometer to the device. The device can then create custom feature sets based on the specified orientations.

In some embodiments, rather than maintaining a number of feature sets representing each possible orientation, non-linear dimensionality reduction (NLDR) can be employed. NLDR involves generating a reduced-dimension representation of the accelerometer data. For example, if the accelerometer data representing a known movement is typically modeled in three dimensions (x, y, and z), NLDR techniques can be employed to generate a two dimensional representation of the known movement.

When modeled in three dimensions, each orientation of the accelerometer may generate a unique representation (i.e. feature set). However, when NLDR is applied to reduce the three dimensional representation into a two dimensional representation, a common two dimensional representation can be employed to represent a known movement in accelerometer data generated by an accelerometer in any orientation. In other words, if eight different three dimensional representations are generated when the accelerometer is worn in eight different orientations, these eight different three dimensional orientations can all be represented by a single (or at least fewer) two dimensional representations. NLDR can be employed to create a single two dimensional representation that commonly represents multiple three dimensional representations. This two dimensional representation for the various orientations can be used as the feature set for the known activity in each of these various orientations.

Figure 5C:
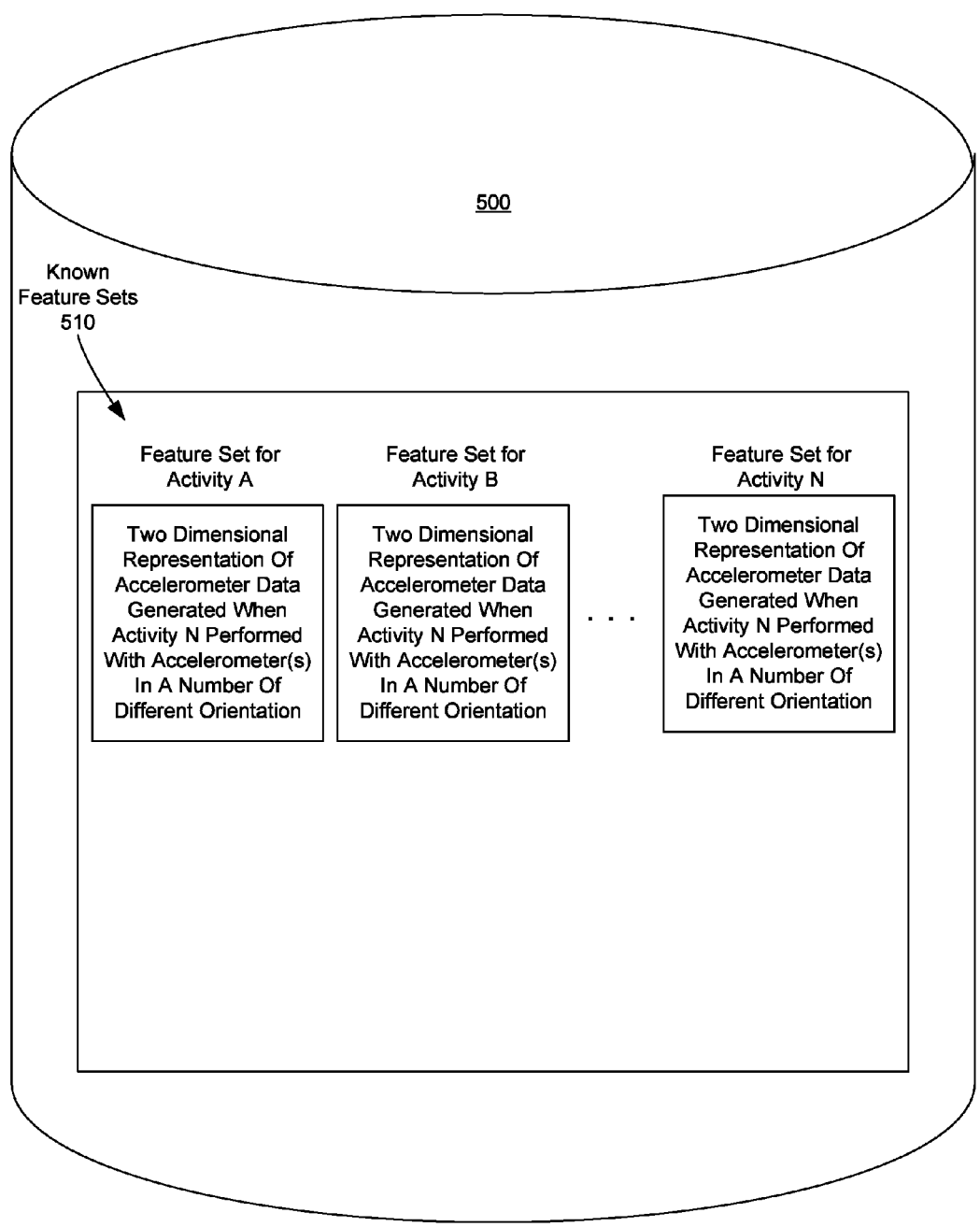
FIG. 5C illustrates an exemplary database that stores feature sets comprising common representations of multiple orientations.

In this way, it would not be necessary to maintain a feature set for each possible orientation as described above because the accelerometer data could be processed using NLDR to generate a two dimensional representation. The generated two dimensional representation could then be compared to the stored two dimensional representations of known movements (i.e. feature sets) to determine which movement was performed. FIG. 5C illustrates an example of database 500 when the feature set for an activity comprises a two dimensional representation common to multiple orientations. As can be seen, the number of feature sets required to identify known movements is reduced when two dimensional representations are used.

Accordingly, in some embodiments, the present invention can identify a known movement from accelerometer data regardless of the orientation of the accelerometer used to generate the accelerometer data by employing NLDR to reduce the accelerometer data into a common two dimensional representation.

Portable Devices Having Detachable Accelerometers

Figure 7A:
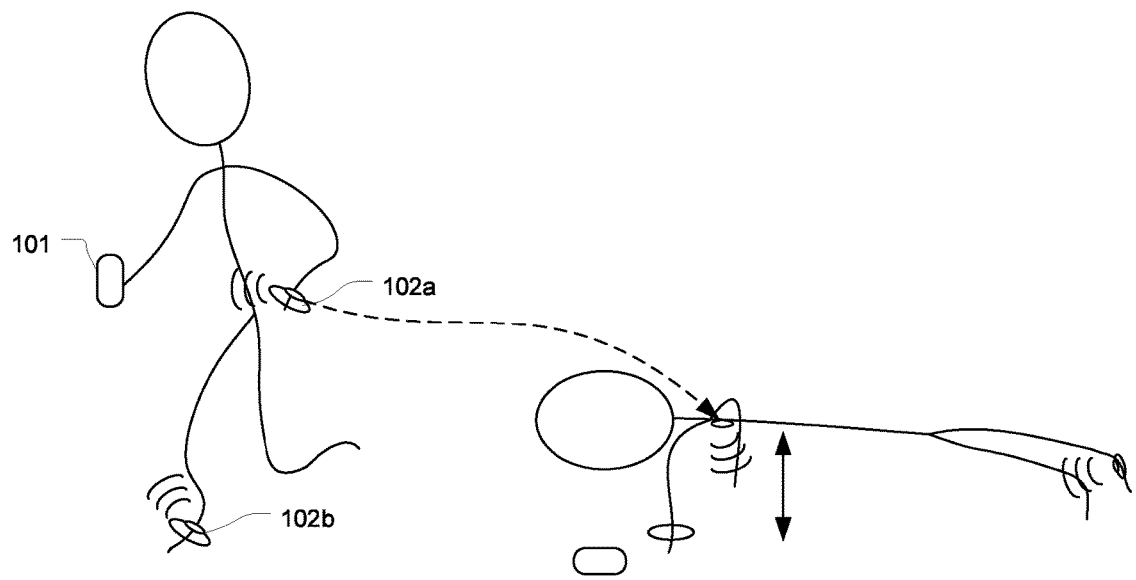
FIGS. 7A and 7B illustrate examples of how a detachable accelerometer can be used.
Figure 7B:
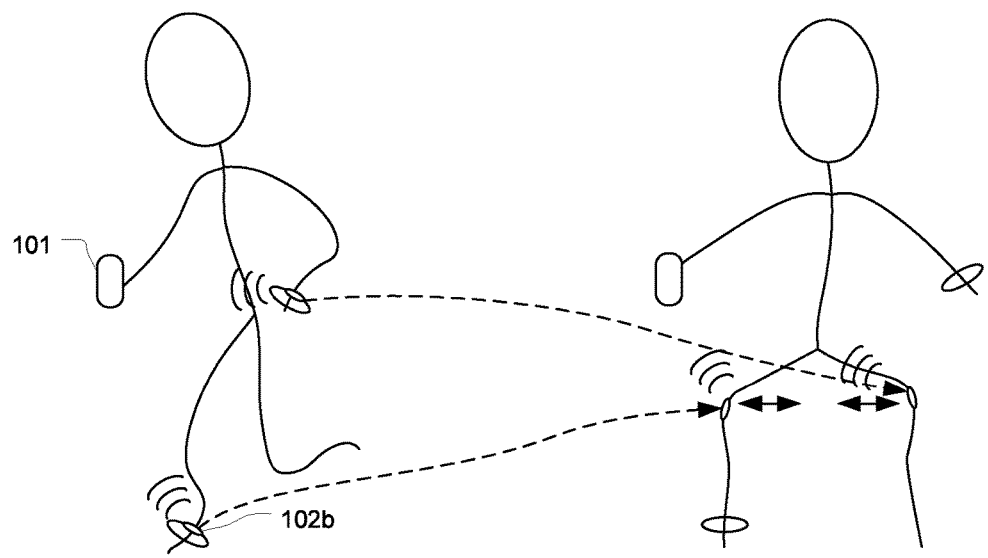

FIGS. 7A and 7B illustrate examples of how a portable accelerometer device can include one or more detachable accelerometers. Both FIGS. 7A and 7B illustrate that a user is wearing two portable accelerometer devices 102a and 102b as shown in FIG. 1. Devices 102a and 102b can be in the form of a bracelet, shoe clip, or other structure wearable by the user.

As shown in FIGS. 7A and 7B, either or both portable accelerometer devices 102a and 102b can include a removable accelerometer. For example, FIG. 7A shoes that the accelerometer of portable accelerometer device 102a is removable from the device to allow the accelerometer to be placed virtually anywhere on the user's body. In the example of FIG. 7A, the accelerometer is placed on the user's chest while the user is performing pushups (e.g. to better measure the up and down motion of the user's chest). In FIG. 7A, portable accelerometer device 102b is left unchanged on the user's ankle/shoe.

FIG. 7B is similar to FIG. 7A except that the accelerometer from both devices 102a and 102b are removed and attached to the user's knees. In this example, the user has placed the accelerometers in a position to accurately identify and measure a hip adduction movement. As shown, both devices 102a and 102b (without the accelerometers) remain on the user's wrist and ankle/foot. In some embodiments, either device could be removed without affecting the ability of the accelerometers to transmit data to portable computing device 101. In contrast, in some embodiments, an accelerometer can be configured to transmit data back to the device from which it was removed to allow the device to transmit the data to portable computing device 101. Also, in some embodiments, these devices can contain one or more other accelerometers (whether fixed or removable) that can continue to function even when the removable accelerometers are removed and used elsewhere.

Accordingly, FIGS. 7A and 7B illustrate portable accelerometer devices that contain a removable accelerometer to allow the user to place the accelerometer at any location on the body to track standard or custom movements. Although these figures show a single accelerometer per device, in some embodiments, a portable accelerometer device can include more than one accelerometer with one or more of the accelerometers being detachable.

In some embodiments, an accelerometer on a portable accelerometer device can be configured to generate accelerometer data both while attached to and detached from the device. In other embodiments, one or more accelerometers on a portable accelerometer device can be inactive until detached from a device. For example, a bracelet can contain two accelerometers where only one is active while attached to the bracelet. In such cases, when an inactive accelerometer is detached, it can become active to enable the accelerometer to be used to track movement on another position of the body.

In some embodiments, portable computing device 101 can be configured with one or more detachable accelerometers. For example, if portable computing device 101 is a mobile phone, an accelerometer can be configured to be attached to the mobile phone and then removed as desired for use on a desired part of the body to track movement. In such cases, the mobile phone can also be configured to receive accelerometer data from one or more portable accelerometer devices independently of or in addition to accelerometer data from the detachable accelerometer.

In other embodiments, a portable accelerometer device can include one or more accelerometers and one or more physiological sensors that are permanently housed in the device, while also including one or more detachable accelerometers that can be removed and used on any desired location of the user's body. Once the user has finished using the detachable accelerometers, they can be returned to the portable accelerometer device for storage, data transmission, charging, etc.

In some embodiments, a portable accelerometer device can be customizable by adding any of a variety of sensors. For example, if the portable accelerometer device is a bracelet, the bracelet can be configured (e.g. with one or more ports, connectors, or the like) to receive one or more sensors such as an accelerometer, a skin sensor, a blood glucose monitor, or any other type of physiological sensor. Each sensor can be configured with a similar adapter so that the user can connect virtually any combination of sensors to the portable accelerometer device.

In some cases, the portable accelerometer device can act as a central hub for the selected sensors such as for routing data to portable computing device 101, charging the sensors, etc. In this way, the user can customize the functionality provided by the portable accelerometer device in a modular fashion.

Although the above description has primarily described the processing of accelerometer data being performed by portable computing device 101, the present invention can equally be implemented when some or all of the processing of the accelerometer data occurs at a server to which portable computing device 101 routes the accelerometer data. In other words, once portable computing device 101 receives accelerometer data from one or more accelerometers, it may perform minimal or no processing on the data and then route the data to one or more servers (i.e. to the cloud) for processing. Results of this processing can then be returned to portable computing device 101. In either case, the implementation of the invention is very similar. With current processing capabilities of many mobile devices, it may be preferred to perform much of the processing in the cloud.

Further, although the description and claims describe that the accelerometers are worn on the user's body, the invention can equally be carried out when an accelerometer is not placed directly on the user's body but on a component being moved by the user's body (e.g. the pedals of a bike, the handles of a weight lifting machine, etc.) or a component that the user's body contacts which may not be moved during an activity (e.g. the handlebars of a bike, the handle of a jogging stroller, etc.). Accordingly, in the claims below, the recitation of the accelerometers being worn at multiple locations of the user's body should be construed to encompass implementations where an accelerometer is not placed directly on a location of the user's body but on a component that the location of the user's body contacts. For example, the invention can be carried out in the same manner to identify that a user is biking whether an accelerometer is worn on a shoe (e.g. as a shoe clip) or attached directly to a bike pedal. In either case, the motion detected by the accelerometer would be the same because the shoe and the pedal follow the same circular path.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed:

1. A method implemented on a computing device for synchronizing data received from multiple accelerometers, the method comprising:
   receiving, at the computing device, multiple streams of accelerometer data generated by multiple accelerometers worn by a user at multiple locations of the user's body while the user performs a first activity;
   accessing one or more timestamps in each of the multiple streams;
   based on the timestamps in each stream, extracting portions of each stream that have a common timestamp indicating that the accelerometer data in the extracted portions was generated during the same time period while the user is performing the first activity; and
   using the extracted portions of each stream that share a common timestamp to identify an entry in a database that represents the first activity, the entry including data representing varying accelerations that are generated at each of the multiple locations of the body when the first activity is performed, whereby the varying accelerations from the database entry are matched to each of the extracted portions of each stream to synchronize the first activity as recorded by each stream.

2. The method of claim 1, further comprising:
   detecting that one or more of the multiple streams is misaligned with one or more other streams; and
   aligning the one or more of the multiple streams with the one or more other streams.

3. The method of claim 2, wherein detecting that one or more of the multiple streams is misaligned with one or more other streams comprises independently processing each of the multiple streams to identify a known movement.

4. The method of claim 3, wherein processing each of the multiple streams to identify a known movement comprises identifying a number of repetitions of the known movement that are represented in each of the multiple streams.

5. The method of claim 2, wherein aligning the one or more of the multiple streams with the one or more other streams comprises time shifting the accelerometer data of at least one of the multiple streams.

6. The method of claim 5, wherein detecting that one or more of the multiple streams is misaligned with one or more other streams comprises:
   independently processing each of the multiple streams to identify the occurrence of a first repetition of a known movement in each of the multiple streams; and wherein the accelerometer data of at least one of the multiple streams is time shifted to cause the occurrence of the first repetition of the known movement in each of the multiple streams to be aligned.

7. The method of claim 6, wherein the accelerometer data of at least one of the multiple streams is time shifted forward and the accelerometer data of at least one of the multiple streams is time shifted backward.

8. The method of claim 1, wherein the multiple streams include streams of accelerometer data generated for multiple axes by the same accelerometer.

9. The method of claim 1, wherein the method is performed by one or more servers which receive the multiple streams of accelerometer data from a portable computing device, the portable computing device having received the multiple streams of accelerometer data from the multiple accelerometers.

10. A method implemented on a computing device for synchronizing data received from multiple accelerometers, the method comprising:
    receiving, at the computing device, multiple streams of accelerometer data generated by one or more multi-axis accelerometers worn by a user while the user performs a first activity, each stream representing one axis of data from one accelerometer;
    accessing one or more timestamps in each of the multiple streams;
    based on the timestamps in each stream, extracting portions of each stream that have a common timestamp indicating that the accelerometer data in the extracted portions was generated during the same time period while the user is performing the first activity; and
    using the extracted portions of each stream that share a common timestamp to identify an entry in a database that represents the first activity, the entry including data representing varying accelerations that are generated at each axis at each location of the body for each accelerometer when the first activity is performed, whereby the varying accelerations from the database entry are matched to each of the extracted portions of each stream to synchronize the first activity as recorded by each stream.

11. The method of claim 10, further comprising:
    detecting that one or more of the multiple streams is misaligned with one or more other streams; and
    aligning the one or more of the multiple streams with the one or more other streams.

12. The method of claim 11, wherein detecting that one or more of the multiple streams is misaligned with one or more other streams comprises independently processing each of the multiple streams to identify a known movement.

13. The method of claim 12, wherein processing each of the multiple streams to identify a known movement comprises identifying a number of repetitions of the known movement that are represented in each of the multiple streams.

14. The method of claim 11, wherein aligning the one or more of the multiple streams with the one or more other streams comprises time shifting the accelerometer data of at least one of the multiple streams.

15. The method of claim 14, wherein detecting that one or more of the multiple streams is misaligned with one or more other streams comprises:
    independently processing each of the multiple streams to identify the occurrence of a first repetition of a known movement in each of the multiple streams; and wherein the accelerometer data of at least one of the multiple streams is time shifted to cause the occurrence of the first repetition of the known movement in each of the multiple streams to be aligned.

16. A method for synchronizing data received from multiple accelerometers, the method being implemented on a server and comprising:
    receiving, at the server from a portable computing device, multiple streams of accelerometer data generated by multiple accelerometers worn by a user at multiple locations of the user's body while the user performs a first activity, the multiple streams of accelerometer data having been received by the portable computing device from the multiple accelerometers;

accessing one or more timestamps in each of the multiple streams;

based on the timestamps in each stream, extracting portions of each stream that have a common timestamp indicating that the accelerometer data in the extracted portions was generated during the same time period while the user is performing the first activity; and using the extracted portions of each stream that share a common timestamp to identify an entry in a database that represents the first activity, the entry including data representing varying accelerations that are generated at each of the multiple locations of the body when the first activity is performed, whereby the varying accelerations from the database entry are matched to each of the extracted portions of each stream to synchronize the first activity as recorded by each stream.

17. The method of claim 16, further comprising:

detecting that one or more of the multiple streams is misaligned with one or more other streams; and aligning the one or more of the multiple streams with the one or more other streams.

18. The method of claim 17, wherein detecting that one or more of the multiple streams is misaligned with one or more other streams comprises:

identifying a known movement in each of the streams; and identifying a time shift between the known movement in the one or more misaligned streams and the known movement in the one or more other streams.

19. The method of claim 17, wherein detecting that one or more of the multiple streams is misaligned with one or more other streams comprises:

identifying a similar number or duration of movements in each of the streams; and identifying a time shift between initiation of the number or duration of movements in the one or more misaligned streams and initiation of the number or duration of movements in the one or more other streams.

20. The method of claim 17, wherein aligning the one or more of the multiple streams with the one or more other streams comprises determining a plurality of possible offsets to apply to each stream and then determining which set of offsets yields a greatest correlation between the multiple streams.

* * * * *